US008690946B2

(12) United States Patent
Baumgartner et al.

(10) Patent No.: US 8,690,946 B2
(45) Date of Patent: *Apr. 8, 2014

(54) INTERVERTEBRAL IMPLANT

(71) Applicant: DePuy Synthes Products, LLC, Raynham, MA (US)

(72) Inventors: Daniel Baumgartner, Oensingen (CH); Martin Wymann, Oberdorf (CH); Mario Gago Ho, Solothurn (CH); Adrian Burri, Brig (CH)

(73) Assignee: DePuy Synthes Products, LLC, Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/733,336

(22) Filed: Jan. 3, 2013

(65) Prior Publication Data

US 2013/0138215 A1    May 30, 2013

Related U.S. Application Data

(63) Continuation of application No. 12/827,376, filed on Jun. 30, 2010, now Pat. No. 8,382,838, which is a continuation of application No. 12/198,761, filed on Aug. 26, 2008, now abandoned, which is a continuation of application No. 10/553,495, filed as application No. PCT/CH03/00247 on Apr. 14, 2003, now Pat. No. 7,429,270.

(51) Int. Cl.
*A61F 2/44* (2006.01)

(52) U.S. Cl.
USPC .................. 623/17.15; 623/17.12; 623/17.13

(58) Field of Classification Search
USPC ............................................ 623/17.11–17.16
See application file for complete search history.

(56) References Cited

U.S. PATENT DOCUMENTS

| 3,867,728 | A | 2/1975 | Stubstad et al. |
| 4,911,718 | A | 3/1990 | Lee et al. |
| 4,932,969 | A | 6/1990 | Frey et al. |
| 5,071,437 | A | 12/1991 | Steffee |
| 5,171,281 | A | 12/1992 | Parsons et al. |
| 5,314,477 | A | 5/1994 | Marnay |
| 5,370,697 | A | 12/1994 | Baumgartner |
| 5,534,030 | A | 7/1996 | Navarro et al. |
| 5,545,229 | A | 8/1996 | Parsons et al. |
| 5,697,969 | A | 12/1997 | Schmitt et al. |
| 6,063,121 | A | 5/2000 | Xavier et al. |
| 6,120,539 | A | 9/2000 | Eldridge et al. |

(Continued)

FOREIGN PATENT DOCUMENTS

| EP | 0346129 | 12/1989 |
| EP | 0346129 A1 | 12/1989 |

(Continued)

OTHER PUBLICATIONS

U.S. Appl. No. 60/375,286, filed Jan. 24, 2002, Ferree.

(Continued)

*Primary Examiner* — Andrew Yang
(74) *Attorney, Agent, or Firm* — Baker & Hostetler LLP

(57) ABSTRACT

An intervertebral implant having an upper and a lower closing plate designed to engage the vertebral end plates. The implant has a deformable body between the closing plates. Between the deformable body and closing plates are cover plates. A plurality of fiber windings run between the cover plates to hold together the cover plates and the deformable body.

18 Claims, 4 Drawing Sheets

(56) References Cited

U.S. PATENT DOCUMENTS

| | | | |
|---|---|---|---|
| 6,419,704 | B1 | 7/2002 | Ferree |
| 6,533,817 | B1 | 3/2003 | Norton et al. |
| 6,626,943 | B2 | 9/2003 | Eberlein et al. |
| 6,645,248 | B2 | 11/2003 | Casutt |
| 6,733,532 | B1 | 5/2004 | Gauchet et al. |
| 6,733,533 | B1 | 5/2004 | Lozier |
| 6,893,465 | B2 | 5/2005 | Huang |
| 6,936,071 | B1 | 8/2005 | Marnay et al. |
| 7,060,097 | B2 | 6/2006 | Fraser et al. |
| 7,066,960 | B1 | 6/2006 | Dickman |
| 7,153,325 | B2 | 12/2006 | Kim et al. |
| 7,156,848 | B2 | 1/2007 | Ferree |
| 7,429,270 | B2 | 9/2008 | Baumgartner et al. |
| 7,563,284 | B2 | 7/2009 | Coppes et al. |
| 7,563,286 | B2 | 7/2009 | Gerber et al. |
| 7,776,092 | B2 | 8/2010 | Lee et al. |
| 8,382,838 | B2 | 2/2013 | Baumgartner et al. |
| 2002/0016595 | A1 | 2/2002 | Michelson |
| 2002/0123750 | A1 | 9/2002 | Eisermann et al. |
| 2002/0169508 | A1 | 11/2002 | Songer et al. |
| 2003/0045939 | A1 | 3/2003 | Casutt |
| 2003/0135277 | A1 | 7/2003 | Bryan et al. |
| 2003/0199984 | A1 | 10/2003 | Trieu |
| 2004/0243238 | A1 | 12/2004 | Arnin et al. |
| 2005/0027364 | A1 | 2/2005 | Kim et al. |
| 2005/0197702 | A1 | 9/2005 | Coppes et al. |
| 2005/0228500 | A1 | 10/2005 | Kim et al. |
| 2007/0270952 | A1 | 11/2007 | Wistrom et al. |
| 2009/0054989 | A1 | 2/2009 | Baumgartner et al. |

FOREIGN PATENT DOCUMENTS

| | | |
|---|---|---|
| EP | 0974319 | 1/2000 |
| FR | 2747034 | 10/1997 |
| WO | WO 90/00374 | 1/1990 |
| WO | WO 93/16664 | 9/1993 |
| WO | WO 01/01893 | 1/2001 |
| WO | WO 02/17825 | 3/2002 |
| WO | WO 2004/089257 | 10/2004 |
| WO | WO 2004/089257 A1 | 10/2004 |

OTHER PUBLICATIONS

"Amended Complaint", In the United States District Court for the District of Delaware, Case No. 08-838-SLR, filed Jan. 2, 2009, 17 pages.

"Civil Docket Sheet", In the United States District Court for Northern District of California San Jose Division, Case No. 5:09-CV-01201 RMW, Mar. 19, 2009, 53 pages.

"Declaration of Allan W. Jansen in Support of Spinal Kinetics, Inc.'s Motion for Summary Judgment of Invalidity of Claims 29-31 of U.S. Patent No. 7,429,270 Under 35 U.S.C. § 112, ¶1", In the United States District Court for Northern District of California San Jose Division, Case No. 5:09-CV-01201 RMW, Mar. 7, 2011, 280 pages.

"Declaration of Allan W. Jansen in Support of Spinal Kinetics, Inc.'s Opposition to Synthes' Partial Motion for Summary Judgment Dismissing Spinal Kinetics' Anticipation and Obviousness Defenses and Cross-Motion for Summary Judgment of Invalidity Under § 102(B) Based on Public Accessibility of Inventors' Thesis Work", with Exhibits, In the United States District Court for Northern District of California San Jose Division, Case No. 5:09-CV-01201 RMW, Jun. 29, 2011, 476 pages.

"Declaration of Andreas Aebi Regarding Translation of Aspects of Burri/Baumgartner Thesis", In the United States District Court for Northern District of California San Jose Division, Case No. 5:09-CV-01201 RMW, Jan. 21, 2011, 5 pages.

"Declaration of Beat Lechmann Responsive to Spinal Kinetics, Inc.'s Cross-Motion "Reply" and Submission of English Translation of Olson Declaration Exhibit 9", with Exhibits, In the United States District Court for Northern District of California San Jose Division, Case No. 5:09-CV-01201 RMW, Jul. 28, 2011, 11 pages.

Declaration of David Koch in Support of Plaintiff's Brief in Opposition to Motion for Summary Judgment of Invalidity of Claims 29-31 Under 35 U.S.C. § 112(1) (Best Mode), In the United States District Court for Northern District of California San Jose Division, Case No. 5:09-CV-01201 RMW, Jan. 21, 2011, 15 pages.

"Declaration of Dr. Beat Gasser", In the United States District Court for Northern District of California San Jose Division, Case No. 5:09-CV-01201 RMW, Jun. 10, 2011, 4 pages.

"Declaration of Dr. Casey E. Lee in Support of Spinal Kinetics Opposition Brief to Synthes' Motion for Partial Summary Judgment Dismissing Invalidity Defenses Based on 35 USC § 112 and § 101", with Exhibits, In the United States District Court for Northern District of California San Jose Division, Case No. 5:09-CV-01201 RMW, Jun. 29, 2011, 49 pages.

Declaration of Ehab M. Samuel in Support of Spianl Kinetics' Motion for Partial Summary Judgment That Each of Claims 29-31 of U.S. Patent No. 7,429,270 Is Not Entitled to the Effective Filing Date of the PCT Application Under 35 U.S.C. § 120, In the United States District Court for Northern District of California San Jose Division, Case No. 5:09-CV-01201 RMW, Jun. 10, 2011, 305 pages.

Declaration of Ehab M. Samuel in Support of Spinal Kineticss, Inc's Reply Brief in Support of Motion for Summary Judgment of Invalidity of Claims 29-31 of U.S. Patent No.7,429,270 Under 35 U.S.C. § 112, ¶1, In The United States District Court for Northern District of California San Jose Division, Case No. 5:09-CV-01201 RMW, Mar. 7, 2011, 27 pages.

"Declaration of James W. Geriak in Support of Spinal Kinetics Inc. Motion for Partial Summary Judgment Dismissing Invalidity Defenses Based on 35 USC §§ 112 and 101", with Exhibits, in The United States District Court for Northern District of California San Jose Division, Case No. 5:09-CV-01201 RMW, Jun. 29, 2011, 836 pages.

"Declaration of James W. Geriak in Support of Spinal Kinetics, Inc.'s Reply in Support of Its Motion for Partial Summary Judgment That Each of Claims 29-31 of U.S. Patent No.7,429,270 is Not Entitled to the Effective Filing Date of the PCT Application Under 35 USC 120", with Exhibits, In the United States District Court for Northern District of California San Jose Division, Case No. 5:09-CV-01201 RMW, Jul. 8, 2011, 247 pages.

Declaration of Jeffrey M. Olson in Support of Plaintiff's Brief in Opposition to Motion for Summary Judgment of Invalidity of Claims 29-31 Under 35 U.S.C. § 112(1) (Best Mode), In the United States District Court for Northern District of California San Jose Division, Case No. 5:09-CV-01201 RMW, Jan. 12, 2011, 73 pages.

"Declaration of Jeffrey M. Olson in Support of Plaintiffs' Motion for Partial Summary Judgment Dismissing Spinal Kinetics' Anticipation and Obviousness Defenses and Motion For Summary Judgment Dismissing Invalidity Defenses Based on 35 U.S.C. § 112 (Written Description, Enablement, Indefiniteness, Best Mode) and § 101 (Utility)", with Exhibits, In the United States District Court for Northern District of California San Jose Division, Case No. 5:09-CV-01201 RMW, Jun. 10, 2011, 559 pages.

Declaration of Kay D. Conerly in Support of Spinal Kinetics' Motion for Partial Summary Judgment That Each of Claims 29-31 of U.S. Patent No. 7,429,270 Is Not Entitled to the Effective Filing Date of the PCT Application Under 35 U.S.C. § 120, In The United States District Court for Northern District of California San Jose Division, Case No. 5:09-CV-01201 RMW, Jun. 10, 2011, 18 pages.

"Declaration of Marc C. Levenston Ph.D. in Support of Spinal Kinetics' Opposition Brief to Synthes' Motion for Partial Summary Judgment Dismissing Invalidity Defenses Based on 35 USC § 112 and § 101", with Exhibits, In the United States District Court for Northern District of California San Jose Division, Case No. 5:09-CV-01201 RMW, Jun. 29, 2011, 36 pages.

"Declaration of Michael L. Reo in Support of Spinal Kinetics Opposition Brief to Synthes' Motion for Partial Summary Judgment Dismissing Invalidity Defenses Based on 35 USC §§ 112 and 101", with Exhibits, In the United States District Court for Northern District of California San Jose Division, Case No. 5:09-CV-01201 RMW, Jun. 29, 2011, 8 pages.

Declaration of Michael L. Reo in Support of Spinal Kinetics' Motion for Partial Summary Judgment That Each of Claims 29-31 of U.S. Patent No. 7,429,270 Is Not Entitled to the Effective Filing Date of

(56) References Cited

OTHER PUBLICATIONS the PCT Application Under 35 U.S.C. § 120, In the United States District Court for Northern District of California San Jose Division, Case No. 5:09-CV-01201 RMW, Jun. 10, 2011, 35 pages.
Declaration of Nicholas C. Koske in Support of Spinal Kinetics' Motion for Partial Summary Judgment That Each of Claims 29-31 of U.S. Patent No. 7,429,270 Is Not Entitled to the Effective Filing Date of the PCT Application Under 35 U.S.C. § 120, In The United States District Court for Northern District of California San Jose Division, Case No. 5:09-CV-01201 RMW, Jun. 10, 2011, 20 pages.
"Declaration of Paul Meier in Support of Plaintiffs' Opposition to Spinal Kinetics' Motion for Summary Judgment That Each of Claims 29-31 of U.S. Patent No. 7,429,270 Is Not Entitled to the Effective Filing Date of the PCT Application Under 35 U.S.C. § 120", In The United States District Court for Northern District of California San Jose Division, Case No. 5:09-CV-01201 RMW, Jun. 29, 2011, 33 pages.
Declaration of Paul Meier in Support of Plaintiffs' Reply in Support of Motion (DKT. 225) for Partial Summary Judgment Dismissing Invalidity Defenses Based on 35 U.S.C. § 112 (Written Description, Enablement, Indefiniteness, Best Mode) and § 101 (Utility), with Exhibits, In The United States District Court for Northern District of California San Jose Division, Case No. 5:09-CV-01201 RMW, Jul. 8, 2011, 46 pages.
"Declaration of Thomas Afzal in Support of Spinal Kinetics Opposition Brief to Synthes Motion for Partial Summary Judgment Dismissing Invalidity Defenses Based on 35 U.S.C. §§ 112 and 101", with Exhibits, In The United States District Court for Northern District of California San Jose Division, Case No. 5:09-CV-01201 RMW, Jun. 29, 2011, 51 pages.
Declaration of Thomas Afzal in Support of Spinal Kinetics' Motion for Partial Summary Judgment That Each of Claims 29-31 of U.S. Patent No. 7,429,270 Is Not Entitled to the Effective Filing Date of the PCT Application Under 35 U.S.C. § 120, In The United States District Court for Northern District of California San Jose Division, Case No. 5:09-CV-01201 RMW, Jun. 10, 2011, 51 pages.
"Defendant Spinal Kinetics, Inc.'s Reply in Support of Its Cross Motion for Summary Judgment of Invalidity Under § 102(B) Based on Public Accessibility of Inventors' Thesis Work", In the United States District Court for Northern District of California San Jose Division, Case No. 5:09-CV-01201 RMW, Jul. 15, 2011, 6 pages.
"Defendant Spinal Kinetics, Inc.'s Trial Brief", In The United States District Court for Northern District of California San Jose Division, Case No. 5:09-CV-01201 RMW, Sep. 1, 2011, 5 pages.
"Defendant's Responsive Claim Construction Brief (Patent L.R. 4-5(b))", In The United States District Court Northern District of California, Case No. C-09-01201 RMW, Jan. 13, 2010, 35 pages.
"Exhibit A Patent Local Rule 3-1(c) Infringement Chart", Jul. 2009, 16 pages.
"Expert Report of Nicholas C. Koske (Redacted)", In the United States District Court for Northern District of California San Jose Division, Case No. 5:09-CV-01201 RMW, May 5, 2011, 74 pages.
"Expert Report of Thomas F. Smegal, Jr.", In the United States District Court for Northern District of California San Jose Division, Case No. 5:09-CV-01201 RMW, Apr. 14, 2011, 100 pages.
"Federal Express Shipment Detail by Payor Type (Original)", Invoice No. 7-210-76533, Jan. 30, 2006, 1 page.
Motion for Partial Summary Judgment Dismissing Invalidity Defenses Based on 35 U.S.C. § 112 (Written Description, Enablement, Indefiniteness, Best Mode) and § 101 (Utility), In The United States District Court for Northern District of California San Jose Division, Case No. 5:09-CV-01201 RMW, Jun. 10, 2011, 30 pages.
"Neuentwicklung eines lumbalen bewegungserhaltenden Bandscheilbenimplantes", EFO-Projekt P01E210, Eidgenössiche Technische Hochschule Zürich, Nov. 14, 2002, 22 pages.
"Notice of Errata in Spinal Kinetics, Inc.'s Opposition to Synthes' Motion for Judgment As a Matter of Law Pursuant to Fed.R.Civ.P. 50(a) (Dkt.502)", In the United States District Court for Northern District of California San Jose Division, Case No. 5:09-CV-01201 RMW, Dec. 27, 2011, 33 pages.

"Opening Expert Report of Casey K. Lee, M.D. with exhibits", Apr. 14, 2011, 67 pages.
"Opening Expert Report of Dr. Marc E. Levenston", Apr. 14, 2011, 62 pages.
"Order Constructing Disputed Claim Language of United States Patent No. 7,429,270", In the United States District Court Northern District of California San Jose Division, Case No. 5:09-CV-01201 RMW, filed Jun. 23, 2010, 20 pages.
"Order Denying Motion for Summary Judgment of Invalidity of Claims 29-31 of U.S. Patent No. 7,429,270 Under 35 U.S.C. § 112", In the United States District Court for Northern District of California San Jose Division, Case No. 5:09-CV-01201 RMW, Feb. 11, 2011, 9 pages.
Order Denying Motion for Summary Judgment of Non-Infringement of Claims 29-31 of U.S. Patent No. 7,429,270, In the United States District Court for Northern District of California San Jose Division, Case No. 5:09-CV-01201 RMW, Jan. 31, 2011, 7 pages.
"Order on Parties' Pretrial Motions", In The United States District Court for Northern District of California San Jose Division, Case No. 5:09-CV-01201 RMW, Aug. 19, 2011, 29 pages.
"Order Re Post-Trial Motions", In the United States District Court for Northern District of California San Jose Division, Case No. 5:09-CV-01201 RMW, Sep. 27, 2012, 20 pages.
"Plaintiff's Amended Complaint", In the United States District Court for the District of Delaware, Case No. 1:08-cv-00839-SLR, Jan. 2, 2009, 17 pages.
"Plaintiff's Brief in Opposition to Motion for Summary Judgment on Non-Infringement by Defendant's Lumbar Disc", In the United States District Court for Northern District of California San Jose Division, Case No. 5:09-CV-01201 RMW, Nov. 5, 2010, 30 pages.
"Plaintiff's Motion for Partial Summary Judgment Dismissing Spinal Kinetics Anticipation and Obviousness Defenses", In the United States District Court for Northern District of California San Jose Division, Case No. 5:09-CV-01201 RMW, Jun. 10, 2011, 30 pages.
"Plaintiff's Reply to Spinal Kinetics, Inc.'s Opposition to Synthes' Renewed Motion for Judgment As a Matter of Law Pursuant to Fed. R. Civ.P.50(b) and for New Trial As to Written Description", In The United States District Court for Northern District of California San Jose Division, Case No. 5:09-CV-01201 RMW, Jun. 18, 2012, 20 pages.
"Plaintiffs' [Proposed] Amended Disclosure of Asserted Claims and Infringement Contentions Under Patent Local Rules 3-1 and 3-2", Exhibit 1, In the United States District Court for Northern District of California San Jose Division, Case No. 5:09-CV-01201 RMW, Jul. 16, 2010, 35 pages.
"Plaintiffs' Brief in Opposition to Motion for Summary Judgment of Invalidity of Claims 29-31 Under 35 U.S.C. § 112(1) (Best Mode)", In the United States District Court for Northern District of California San Jose Division, Case No. 5:09-CV-01201 RMW, filed Jan. 21, 2011, 30 pages.
"Plaintiffs' Brief in Response to Defendant's Supplemental Markman Brief", In The United States District Court for Northern District of California San Jose Division, Case No. 5:09-CV-01201 RMW, Apr. 21, 2010, 12 pages.
"Plaintiffs' Disclosure of Asserted Claims and Infringement Contentions Under Patent Local Rules 3-1 and 3-2", In The United States District Court Northern District of California, Case No. C-09-01201 RMW, Jul. 24, 2009, 9 pages.
"Plaintiffs' Disclosure of Asserted Claims and Infringement Contentions Under Patent Local Rules 3-1 and 3-2—Exhibit A: Patent Local Rule 3-1(c) Infringement Chart", In the United States District Court Northern District of California, Case No. C-09-01201 RMW, Jul. 24, 2009, 16 pages.
"Plaintiffs' Opening Claim Construction Brief (Patent L.R. 4-5(a))", In the United States District Court Northern District of California, Case No. C-09-01201 RMW, Dec. 24, 2009, 43 pages.
"Plaintiffs' Opposition to Spinal Kinetics' Motion for Summary Judgment That Each of Claims 29-31 of U.S. Patent No. 7,429,270 Is Not Entitled to the Effective Filing Date of the PCT Application Under 35 U.S.C. § 120", In The United States District Court for Northern District of California San Jose Division, Case No. 5:09-CV-01201 RMW, Jun. 29, 2011, 31 pages.

(56) References Cited

OTHER PUBLICATIONS

Plaintiffs' Reply Claim Construction Brief (Patent L.R. 4-5(c)), In The United States District Court Northern District of California, Case No. C-09-01201 RMW, Feb. 1, 2010, 37 pages.
"Rebuttal Expert Report of Paul Ducheyne, Ph.D.", May 5, 2011, 87 pages.
"Rebuttal Expert Report of Thomas F. Smegal, Jr.", In The United States District Court for Northern District of California San Jose Division, Case No. 5:09-CV-01201 RMW, May 5, 2011, 10 pages.
"Rebuttal Expert Report of Wilson C. Hayes, Ph.D. Re Dr. Levenston's Non-Infringement Assertions and Related Issues", In The United States District Court for Northern District of California San Jose Division, Case No. 5:09-CV-01201 RMW, May 5, 2011, 9 pages.
"Reply Brief in Support of Plaintiffs' Motion (Dkt .225) for Partial Summary Judgment Dismissing Invalidity Defenses Based on 35 U.S.C. § 112 (Written Description, Enablement, Indefiniteness, Best Mode) and § 101 (Utility)", In The United States District Court for Northern District of California San Jose Division, Case No. 5:09-CV-01201 RMW, Jul. 8, 2011, 21 pages.
"Reply Brief in Support of Plaintiffs' Motion (Dkt. 224) for Partial Summary Judgment Dismissing Spinal Kinetics Anticipation and Obviousness Defenses", In The United States District Court for Northern District of California San Jose Division, Case No. 5:09-CV-01201 RMW, Jul. 8, 2011, 21 pages.
Spinal Kinetics Inc.'s Notice of Motion and Motion for Summary Judgment of Non-Infringement of Claims 29-31 of U.S. Patent No. 7,429,270 by Lumbar Disc of Defendant Spinal Kinetics, Inc., Sep. 13, 2010, 20 pages.
"Spinal Kinetics' Opposition to Synthes' Partial Motion for Summary Judgment Dismissing Spinal Kinetics' Anticipation and Obviousness Defenses and Cross-Motion for Summary Judgment of Invalidity Under §102(B) Based on Public Accessibility of Inventors' Thesis Work", Jun. 29, 2011, 32 pages.
"Spinal Kinetics, Inc.'s Amended Notice Pursuant to 35 U.S.C. § 282", In the United States District Court for Northern District of California San Jose Division, Case No. 5:09-CV-01201 RMW, Oct. 6, 2011, 28 pages.
"Spinal Kinetics, Inc.'s Notice of Motion and Motion for Judgment As a Matter of Law on Invalidity for Lack of Written Description", In The United States District Court for Northern District of California San Jose Division, Case No. 5:09-CV-01201 RMW, Dec. 7, 2011, 12 pages.
"Spinal Kinetics, Inc.'s Notice of Motion and Motion for Judgment As a Matter of Law of Non-Infringement of Claims 29-31 of the '270 Patent Based on the Doctrine of Equivalents-Renewed", In The United States District Court for Northern District of California San Jose Division, Case No. 5:09-CV-01201 RMW, Jan. 10, 2012, 5 pages.
Spinal Kinetics, Inc.'s Notice of Motion, Motion and Memorandum in Support of Motion for Partial Summary Judgment That Each of Claims 29-31 of U.S. Patent No. 7,429,270 Is Not Entitled to the Effective Filing Date of the PCT Application Under 35 U.S.C. § 120, In the United States District Court for Northern District of California San Jose Division, Case No. 5:09-CV-01201 RMW, Jun. 10, 2011, 32 pages.
"Spinal Kinetics, Inc.'s Notice of Motion, Motion, and Memorandum in Support of Motion for Summary Judgment of Invalidity of Claims 29-31 of U.S. Patent No. 7,429,270 Under 35 U.S.C. § 112, ¶1", In the United States District Court for Northern District of California San Jose Division, Case No. 5:09-CV-01201 RMW, Mar. 7, 2011, 29 pages.
Spinal Kinetics, Inc.'s Objections to the Declaration of David Koch in Support of Synthes' Opposition to Spinal Kinetic's Motion for Summary Judgment of Invalidity of Claims 29-31 of U.S. Patent No. 7,429,270 Under 35 U.S.C. § 112, ¶1, In the United States District Court for Northern District of California San Jose Division, Case No. 5:09-CV-01201 RMW, Mar. 7, 2011, 9 pages.
"Spinal Kinetics, Inc.'s Opposition Brief to Synthes' Motion for Partial Summary Judgment Dismissing Invalidity Defenses Based on 35 U.S.C. § 112 and § 101", In The United States District Court for Northern District of California San Jose Division, Case No. 5:09-CV-01201 RMW, Jun. 29, 2011, 30 pages.
"Spinal Kinetics, Inc.'s Opposition to Synthes' Motion for Judgment As a Matter of Law Pursuant to Fed R. Civ.P. 50(a)", In the United States District Court for Northern District of California San Jose Division, Case No. 5:09-CV-01201 RMW, Dec. 21, 2011, 31 pages.
"Spinal Kinetics, Inc.'s Opposition to Synthes' Renewed Motion for Judgment As a Matter of Law Pursuant to Fed. R. Civ. P. 50(b) and for New Trial As to Written Description", In The United States District Court for Northern District of California San Jose Division, Case No. 5:09-CV-01201 RMW, Jun. 4, 2012, 31 pages.
"Spinal Kinetics, Inc.'s Preliminary Invalidity Contentions [Amended]", In the United States District Court Northern District of California San Jose Division, Case No. 5:09-CV-01201 RMW, Dec. 28, 2009, 211 pages.
Spinal Kinetics, Inc.'s Reply Brief in Support of Motion for Summary Judgment of Invalidity of Claims 29-31 of U.S. Patent No. 7,429,270 Under 35 U.S.C. § 112, ¶1, In the United States District Court for Northern District of California San Jose Division, Case No. 5:09-CV-01201 RMW, Mar. 7, 2011, 19 pages.
"Spinal Kinetics, Inc.'s Reply in Support of Its Motion for Partial Summary Judgment That Each of Claims 29-31 of U.S. Patent No. 7,429,270 Is Not Entitled to the Effective Filing Date of the PCT Application Under 35 U.S.C. § 120", In the United States District Court for Northern District of California San Jose Division, Case No. 5:09-CV-01201 RMW, Jul. 8, 2011, 19 pages.
"Spinal Kinetics, Inc.'s Reply in Support of Its Renewed Motion for Judgment As a Matter of Law of Non-Infringement of Claims 29-31 of the '270 Patent Based on the Doctrine of Equivalents", In the United States District Court for Northern District of California San Jose Division, Case No. 5:09-CV-01201 RMW, Jan. 31, 2012, 3 pages.
"Spinal Kinetics, Inc.'s Reply in Support of Supplemental Authorities Regarding Written Description Invalidity Based Solely on the Language of the Patent Specification", In the United States District Court for Northern District of California San Jose Division, Case No. 5:09-CV-01201 RMW, Sep. 7, 2012, 7 pages.
"Spinal Kinetics, Inc.'s Response to Synthes' Surreply Re: Written Description Invalidity Based Solely on the Language of the Patent Specification", In the United States District Court for Northern District of California San Jose Division, Case No. 5:09-CV-01201 RMW, Sep. 20, 2012, 6 pages.
"Spinal Kinetics, Inc.'s Submission of Authorities Re: Written Description Invalidity Based Solely on the Language of the Patent Specification", In the United States District Court for Northern District of California San Jose Division, Case No. 5:09-CV-01201 RMW, Aug. 2, 2012, 5 pages.
"Spinal Kinetics, Inc.'s Second Amended Invalidity Contentions and Exhibits 1-29", In the United States District Court for Northern District of California, Case No. 5:09-CV-01201 RMW, Sep. 30, 2010, 278 pages.
"Spinal Kinetics' Answer to Amended Complaint, Affirmative Defenses, and Counterclaims", In the United States District Court for the District of Delaware, Case No. 08-838-SLR, filed Jan. 20, 2009, 13 pages.
Spinal Kinetics' Memorandum in Reply to Opposition to Motion for Summary Judgment of Non-Infringement of Claims 29-31 of U.S. Patent No. 7,429,270 by Lumbar Disc of Defendant Spinal Kinetics, Inc., In the United States District Court for Northern District of California San Jose Division, Case No. 5:09-CV-01201 RMW, Jan. 7, 2011, 20 pages.
"Spinal Kinetics' Supplemental Markman Brief Re Statements in File History Cannot Alter Statements in the Specification About Embedded Fibers", In the United States District Court for Northern District of California San Jose Division, Case No. 5:09-CV-01201 RMW, Mar. 22, 2010, 7 pages.
"Supplemental Declaration of Jeffrey M. Olson in Support of Plaintiff's Motion for Partial Summary Judgment Dismissing Spinal Kinetics' Anticipation and Obviousness Defenses", with Exhibits, In the United States District Court for Northern District of California San Jose Division, Case No. 5:09-CV-01201 RMW, Jun. 30, 2011, 10 pages.

(56) References Cited

OTHER PUBLICATIONS

"Synthes' Motion for Judgment As a Matter of Law Pursuant to Fed. R. Civ. P. 50(a)", With Exhibits, In the United States District Court for Northern District of California San Jose Division, Case No. 5:09-CV-01201 RMW, Dec. 7, 2011, 32 pages.

"Synthes' Renewed Motion for Judgment As a Matter of Law Pursuant to Fed. R. Civ. P. 50(b) and for New Trial As to Written Description", In the United States District Court for Northern District of California San Jose Division, Case No. 5:09-CV-01201 RMW, May 21, 2012, 27 pages.

"Synthes' Reply in Support of Its Motion for Judgment As a Matter of Law Pursuant to Fed. R. Civ .P. 50(a)", In the United States District Court for Northern District of California San Jose Division, Case No. 5:09-CV-01201 RMW, Dec. 28, 2011, 17 pages.

"Synthes' Response to Spinal Kinetic's, Inc.'s Second Supplemental Written Description Arguments and Authorities", In the United States District Court for Northern District of California San Jose Division, Case No. 5:09-CV-01201 RMW, Sep. 12, 2012, 4 pages.

"Synthes' Response to Spinal Kinetics, Inc.'s Motion for Judgment As a Matter of Law Pursuant to Fed. R. Civ. P. 50(a) of Claims 29-31 of the '270 Patent Based on the Doctrine of Equivalents-Renewed", In the United States District Court for Northern District of California San Jose Division, Case No. 5:09-CV-01201 RMW, Jan. 24, 2012, 3 pages.

"Synthes' Response to Spinal Kinetics, Inc.'s Supplemental Written Description Arguments and Authorities", In the United States District Court for Northern District of California San Jose Division, Case No. 5:09-CV-01201 RMW, Aug. 17, 2012, 7 pages.

"Synthes' Response to Spinal Kinetics, Inc.'s Third Supplemental Written Description Arguments and Authorities", In the United States District Court for Northern District of California San Jose Division, Case No. 5:09-CV-01201 RMW, Sep. 24, 2012, 3 pages.

"Trial Transcript of Casey K. Lee, M.D.", Dec. 1, 2011, 33 pages.

"Trial Transcript of Nicholas C. Koske", Nov. 29, 2011, 32 pages.

"Verdict Form", In the United States District Court for Northern District of California, Case No. C-09-CV-01201 RMW, Dec. 13, 2011, 5 pages.

Baumgartner, "Email re: Intervertebral Disk Prosthesis", Sep. 4, 2006, 1 page.

Burri et al., "Neuentwicklung eines Implantates für den totalen Bandscheibenersatz", Thesis, Swiss Federal Institute of Technology Zurich, Feb. 2002, 98 pages.

Burri et al., "Neuentwicklung eines Implantates für den totalen Bandscheibenersatz", Thesis, Swiss Federal Institute of Technology Zurich, Feb. 2002, 99 pages. (Bates Nos. SYNT 072346-SYNT 072444).

Burri et al., "Neuentwicklung eines Implantates für den totalen Bandscheibenersatz", Thesis, With Library Card, Swiss Federal Institute of Technology Zurich, Feb. 2002, 3 pages (Bates Nos. SYNT 072448-SYNT 072450).

Burri et al., "Neuentwicklung eines Implantates für den totalen Bandscheibenersatz", Thesis, Swiss Federal Institute of Technology Zurich, Feb. 2002, 100 pages (Bates Nos. SYNT 072451-SYNT 072550).

Burri et al., "New Development of a Mobility Conserving Lumbar Disc Implant", Thesis Presentation, Swiss Federal Institute of Technology Zurich, Feb. 25, 2002, 42 pages.

Butscher et al., "Untersuchungsbericht A01G040", Contracting Authority, B. Gasser, Internal Foundational Assignment, Sep. 15, 2004, 24 pages.

Certified English Translation commissioned by Defendant of Kweon et al., "Optimal Design of Synthetic Intervertebral Disc Prosthesis Considering Nonlinear Mechanical Behavior", The Korean Society of Mechanical Engineers Papers Book A, 2002, vol. 26, Issue 2, 234-242.

Certified English Translation of "Neuentwicklung eines lumbalen bewegungserhaltenden Bandscheilbenimplantes", EFO-Projekt P01E210, Eidgenössiche Technische Hochschule Zürich, Nov. 14, 2002, 45 pages.

Certified English Translation of Baumgartner, "Email re: Spinal Kinetics", Sep. 4, 2006, 2 pages.

Certified English Translation of Butscher et al., "Untersuchungsbericht A01G040", Contracting Authority, B. Gasser, Internal Foundational Assignment, Sep. 15, 2004, 25 pages.

Certified English Translation of International Patent Application Publication No. WO 2004/089257 A1 for "Intervertebral Implant", published Oct. 21, 2004, Inventors: Daniel Baumgartner, 21 pages.

English Translation of Burri et al., "Neuentwicklung eines Implantates für den totalen Bandscheibenersatz", Thesis, With Library Card, Swiss Federal Institute of Technology Zurich, Feb. 2002, 98 pages. (Bates Nos. SYNT 072448-SYNT 072450).

English Translation of Burri et al., "New Development of a Mobility Conserving Lumbar Disc Implant", Thesis Presentation, Swiss Federal Institute of Technology Zurich, Feb. 25, 2002, 42 pages.

English Translation of Burri et al., "New Development of an Implant for Total Disc Replacement", Thesis, Swiss Federal Institute of Technology Zurich, Feb. 2002, 197 pages.

Hudgins, "Development and Characterization of a Prosthetic Intervertebral Disc", A Thesis Presented to the Academic Faculty, Georgia Institute of Technology, Nov. 1998, 223 pages.

Hudgins, "Development and Characterization of a Prosthetic Intervertebral Disc", Georgia Institute of Technology, Nov. 1998, 149 pages.

Kim et al., "Adjacent Disc Pressure and Facet Force Comparison for Cervical Spine Arthroplasty with Spinal Kinetics (Elastomer), Prodisc-C (Metal to Uhmwpe), Prestige (Metal Only) Artificial Discs and Anterior Cervical Disectomy and Fusion", Stanford University, Exhibit date Dec. 9, 2010, 1 page.

Kweon et al., "Optimal Design of Synthetic Intervertebral Disc Prosthesis Considering Nonlinear Mechanical Behavior", The Korean Society of Mechanical Engineers Papers Book A, 2002, vol. 26, Issue 2, 234-242.

Spinal Kinetics, "Instructions for Use for Spinal Kinetics Cervical Disc System", © 2006, 19 pages.

Spinal Kinetics, Inc., "SpinalKinetics Motion for Life", © 2006, 1 page.

Spinal Kinetics, Inc., "Transportation Charges for Device and Instrument Shipments", Dec. 18, 2006, 1 page.

Stiftung, "RMS-Bericht 2004", RMS, 2004, 46 pages.

Baumgartner et al., "Invitation to a Seminar with RMS", Feb. 21, 2002, 2 pages.

"Dynesys Dynamic Stabilization System Brochure", Zimmer Spine, Sep. 30, 2013, 8 pages.

"Judgment", In the United States District Court for the Northern District of California, Case No. 5:09 cv 01201 RMW, Apr. 23, 2012, 2 pages.

U.S. Appl. No. 90/020,063, Re-examination of U.S. Patent No. 8,382,838: Revised Request for Re-examination filed on Nov. 29 2013, 455 pages.

"Opinion", United States Court of Appeals for Federal Circuit, Case No. 2013-1047-1059, dated Oct. 29, 2013, 32 pages.

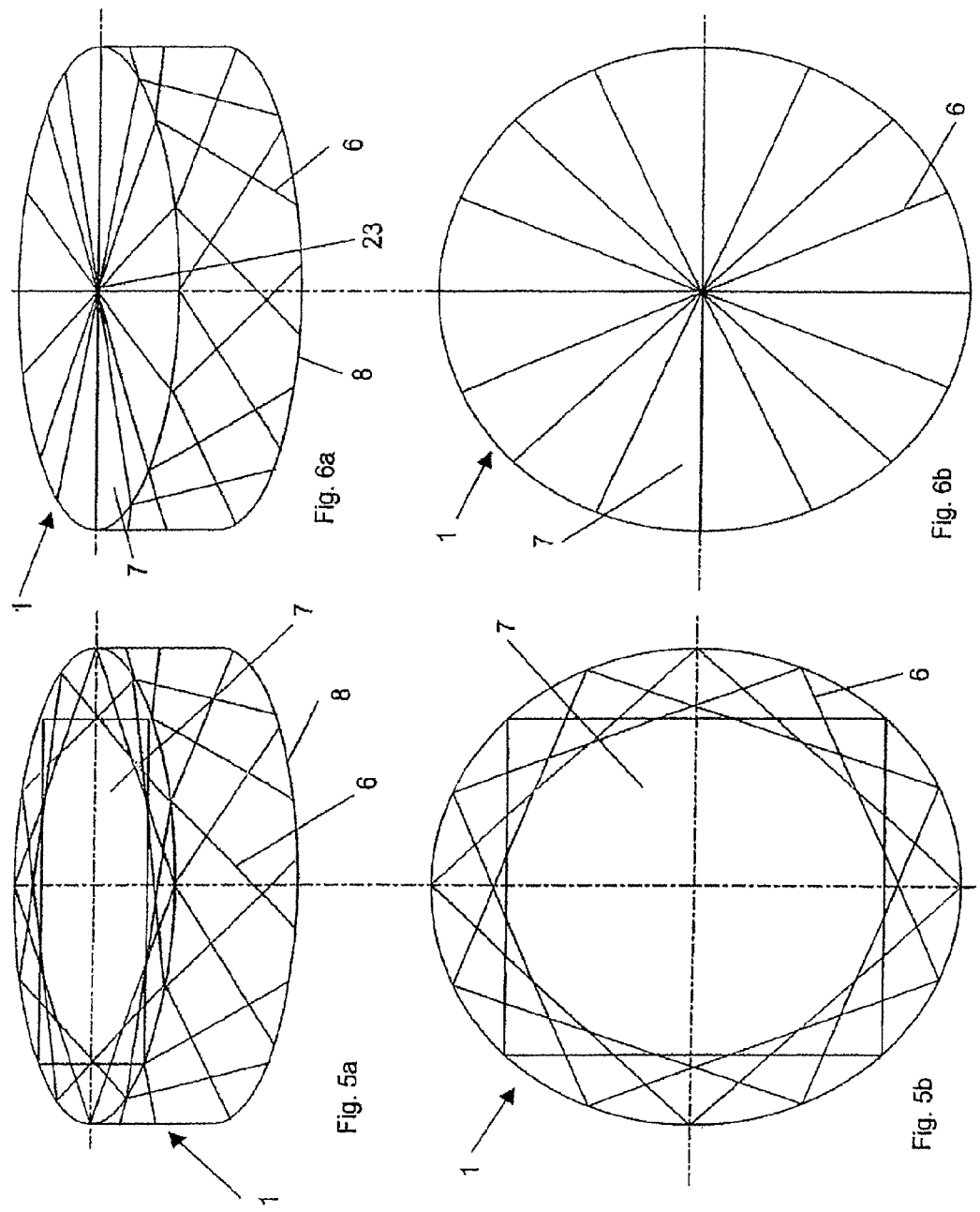

INTERVERTEBRAL IMPLANT

CROSS REFERENCE TO RELATED APPLICATIONS

This application is a continuation of U.S. patent application Ser. No. 12/827,376 filed on Jun. 30, 2010, which is a continuation of U.S. patent application Ser. No. 12/198,761, filed on Aug. 26, 2008, now abandoned, which is a continuation of U.S. patent application Ser. No. 10/553,495, filed on Jul. 25, 2006, now U.S. Pat. No. 7,429,270, which is a National Stage application of PCT/CH03/00247, filed on Apr. 14, 2003, the entire disclosures of which are incorporated herein by reference in their entireties.

TECHNICAL FIELD

The invention concerns an intervertebral implant.

BACKGROUND

An intervertebral disc prosthesis of the generic type is known from U.S. Pat. No. 4,911,718 Lee. This known intervertebral disc prosthesis comprises a central core, that is so formed from a biocompatible elastomer, such that it is roughly equivalent to the nucleus pulpous of a natural intervertebral disc, as well as from a multi-layer laminate from fibres bound in an elastomer, arranged around the core. Each laminate layer has its own yarn system, so that a plurality of fibre groups are present. The fibres of the individual layers have various orientations, whereby the angles of the fibres relative to the central axis of the intervertebral disc are in the range of ±20° and ±50°, preferably 0°, +45° and −45°.

From WO 90/00374 Klaue a hip prosthesis is known, the shaft of which is made from a tubular mesh, i.e. a structure, that comprises at least two series of fibres crossing one another. In this application the interior of the tubular mesh remains empty as the shaft of the femur component.

In the case of the prosthesis disclosed in U.S. Pat. No. 4,911,718 Lee, although the individual fibres are integrated in the laminate that is made from an elastomer or another type of synthetic material, their ends are, however, adhered only to the end plates, so that they do not surround the core and consequently, in the case of a radial expansion of the core, cannot accept any tensile force. When adhering the lateral walls, cut out from the fibrous matrix compound, to the end plate, a fixing of the integrated fibres on the end plate is quite difficult, only the cross-section of the fibre offers a contact surface for the chemical joint. Therefore increased stresses occur especially on these joining places of the fibres on the end plate.

Furthermore, in the case of Lee the length of the individual fibres is only from the bottom cover plate to the top cover plate, what corresponds to the sheathing height or a diagonal of the projected sheathing height. Thus the forces occurring can be reduced only along these lengths due to the transfer of the shearing force of the fibres to the elastomer. Thus positions of increased stresses result at the fixings, i.e. on the ends of the fibres.

The prosthesis disclosed in WO 90/00374 Klaue comprises a system of fibres, the individual fibres of which are not fixed on both ends, as well as there is no deformable core. Therefore in the case of an axial compression of the prosthesis the axial compression forces occurring cannot be transferred as tensile forces to the fibres.

From U.S. Pat. No. 3,867,728 Stubstad et al. an intervertebral disc prosthesis is known, that has an elastomeric sandwich structure with a fibre system. A disadvantage of this known prosthesis is that the fibre system, joined with the cover plates, is either not embedded in the sheathing body or in another embodiment is embedded in a multi-layer laminate of an elastomer.

SUMMARY

This is where the invention wants to provide remedy. The object of the invention is to produce an intervertebral implant, that comprises a fibre system joined with the cover plates, by virtue of which a sheathing body, surrounding the central part and made from a homogeneous material, will be reinforced.

The inventions achieves this objective with an intervertebral implant as described herein.

The basic advantages, achieved by the invention, are that with the intervertebral implant according to the invention the fibre system can be first wound around the central part and following this poured into an elastomer forming the elastic sheathing body, so that the sheathing, enveloping the central part, can be easily produced, by applying the elastic material around the fibre system after its winding, the anchoring of the fibre system is possible by various means, for example also on the opposing inner surfaces of the cover plates, the central part allows a movement of both adjacent bodies of the vertebra in the case of a compression, flexion or extension, lateral bending and torsion, the momentary centre of rotation or the momentary axes of rotation are not determined by the intervertebral implant itself, and they can position themselves according to the rule of minimum forces or moments occurring, by varying the number of fibres in the circumferential direction, the cross-section of the fibres and the choice of material, the behaviour of the intervertebral implant can be so adjusted, that under varying loads the movements occur as in the case of the natural intervertebral disc, and by varying the arrangement and the execution of the fibre system certain movement limitations can be placed on the intervertebral implant, and from a certain deformation a limit region occurs, where despite the further increasing forces no deformation takes place or in the case of moments occurring the implant will no longer tilt.

The axial compression forces occurring under a load on the spinal column are transmitted to the central part via the two end plates. The compression forces deform the central part situated between the two end plates, in particular an elastic formed body possibly present therein, in such a manner that the central part bulges radially. This expansion of the central part is restricted by the fibre system surrounding the central part and the radial compression forces arising can be absorbed by the fibre system as a tensile force. Thus a further, disadvantageous bulging of the central part can be limited. By anchoring the fibre system in both cover plates, the intervertebral implant remains stable even under the greatest loads and the fibre system is capable to withstand even considerable tensile forces.

In a preferred embodiment the entire fibre system is embedded in the elastic sheathing body, so that the fibre system does not necessarily need to be made from a biocompatible material.

In a further embodiment the fibre system is only partially embedded in the elastic sheathing body, while the fibre system has a radial thickness δ relative to the central axis and the elastic sheathing body has a radial thickness d, and the δ/d× 100% ratio is in a range of 80% and 350%. By virtue of this the advantages can be achieved, that the large relative movements in the peripheral region of the cover plates occurring during a flexion/extension movement or a lateral movement of the adjacent bodies of the vertebra are not subjected to a great resistance by the elastic sheathing body and due to this the danger of a fissure formation in the sheathing body is slighter.

The embedding of the fibre system in the elastic sheathing body can be carried out various embodiments in such a manner, that a) the fibre system can be moved relative to the elastic material of the sheathing body, or b) the fibre system cannot be moved relative to the elastic material of the sheathing body.

In yet another embodiment the entire fibre system is anchored on the cover plates, so that greater tensile forces can be accepted by the fibre system, and consequently the intervertebral implant obtains a great torsional rigidity.

In another embodiment the sheathing body, accommodating the fibre system, is made from an elastic, biocompatible material, preferably an elastomer, produced in particular based on polyurethane (PUR). However, silicone rubber, polyethylene, polycarbonate urethane (PCU) or polyethylene terephthalate (PET) may also be used.

In yet another embodiment the central part is filled at least partially with an incompressible medium, preferably a liquid.

In another embodiment the central part comprises an incompressible liquid core and an elastic formed body provided around it, while the liquid can be accommodated, for example, in a cavity provided in the formed body. This brings with it the advantage, that by virtue of the liquid core a mechanical behaviour of the intervertebral implant is similar to that of a physiological intervertebral disc. The axial deformation of the elastic central part will result in the radial expansion of the incompressible liquid and consequently in the radial expansion of the wall of the central part containing the fibre system. The tensile forces, occurring due to the radial expansion or the bulging of the wall of the central part, are basically absorbed by the fibres.

The anchoring of the fibres on the cover plates can be carried out, for example, in the following manner:

a) Mechanically by guiding the fibres designed as continuous fibres through grooves and over the external surfaces of the cover plates from one groove to another one. Thus the fibres surround the central part together with the cover plates. By guiding the fibres in the grooves the fibre system can be so anchored on the cover plates, that in the case of tensile forces acting on the fibres no slipping of the fibres on the lateral sides is possible because the fibres can absorb only tensile forces, b) Mechanically by a wedge-shaped construction of the grooves, so that the fibres extending from cover plate to cover plate can be firmly clamped in the grooves, and/or c) By adhering the fibre system on the cover plates.

In yet another embodiment of the intervertebral implant according to the invention each cover plate comprises on its periphery a lateral surface and grooves distributed on the circumference and radially penetrating into the lateral surfaces. The fibres, part of this fibre system, are guided through these grooves.

In a further embodiment the central part and the fibre system are joined with the cover plates in a form-locking manner.

In yet a further embodiment the fibre system is guided over the external surfaces of both cover plates, so that it will surround the central part as well as the cover plates.

When using an endless fibre, that covers the entire implant, the stresses preferably are distributed on the entire circumference of this winding. The fibre system is preferably in the form of a woven material, fabric or is knitted.

In another embodiment channels are mortised in the external surfaces of the cover plates to accommodate the fibre system.

In yet another embodiment the central part is essentially hollow-cylindrical, hollow-prismatic or is a body of rotation, an ellipsoid, a partial sphere or barrel-shaped with an axis of rotation that is coaxial with the central axis. Such designs secure the advantage that the position of the rotation axes of the adjacent vertebral bodies correspond to the greatest possible extent to those of the natural intervertebral disc.

The fibre system can be made, for example, from UHM-WPE (ultra high molecular weight polyethylene) or from PET (polyethylene terephthalate).

In another embodiment of the intervertebral implant according to the invention, a closing plate intended and designed for contact on the base plate or cover plate of the adjacent vertebral bodies is affixed on each cover plate, each of the said closing plate having an external surface at right angles to the central axis with a macroscopic structure. The structure may be, for example, in the form of teeth. The macroscopic structure allows a primary stabilisation of the intervertebral implant immediately after the operation. Thus a mechanical anchoring of the intervertebral implant at a time when the growing of the bone on the intervertebral implant has not yet taken place, can be achieved.

In yet a further embodiment the woven material is formed from first and second fibres, wherein the first fibres include an angle $\alpha$ with the central axis and the second fibres include an angle $\beta$ with the central axis. The angles for $\alpha$ or $\beta$ are preferably between 15° and 60°.

In another embodiment the first and second fibres are interwoven with one another.

In yet another embodiment the elastic formed body has at right angles to the central axis a cross-sectional surface $F_F$, while the central part has at right angles to the central axis a cross-sectional surface $F_M$ and the $F_F/F_M$ ratio of these two cross-sectional surfaces is between 30% and 65%.

In a further embodiment the elastic formed body is surrounded by a semi-permeable membrane, while in the interior of the elastic formed body preferably physiological table salt solution is present.

With regard to the central axis the fibre system may be single-layered or multi-layered, preferably 2-6 layered. Furthermore, the fibre system can be wound on the elastic formed body. The winding on the elastic formed body can be in two different directions, preferably rotationally symmetrically.

In yet another further embodiment a closing plate can be fastened on each cover plate, the closing plate having at right angles to the central axis an external surface with a macroscopic structure, preferably in the form of teeth.

The diameter of the fibres is in a range of 0.005 mm and 0.025 mm. A yarn (roving) is preferably produced from a plurality of fibres, whereby 500-2000 fibres form a yarn with a cross-sectional surface of 0.5 mm$^2$ to 2 mm$^2$.

In those embodiments, wherein the fibre system has fibre sections crossing one another, in the case of flexion movements (flexion, extension, lateral flexion) of the patients some fibre sections will be unilaterally clamped and in case of shearing the fibre sections extending tangentially to the shearing direction absorb the forces.

BRIEF DESCRIPTION OF THE DRAWINGS

The invention and developments of the invention are explained in detail in the following based on partially schematic illustrations of several embodiments. They show in.

DETAILED DESCRIPTION OF ILLUSTRATIVE EMBODIMENTS

Figure 1:
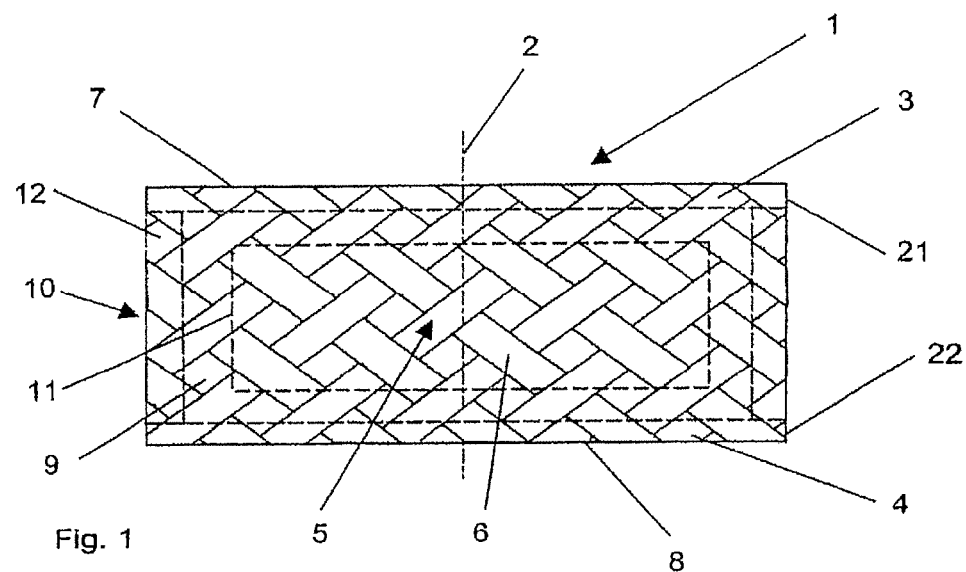
FIG. 1—a side view of an embodiment of the intervertebral implant according to the invention, FIG. 2—a top view on the embodiment of the intervertebral implant according to the invention, illustrated in FIG. 1, FIG. 3—a side view of another embodiment of the intervertebral implant according to the invention, FIG. 4—a section through the embodiment of the intervertebral implant according to the invention, illustrated in FIG. 3, FIG. 5a—a perspective illustration of the fibre system of an embodiment of the intervertebral implant according to the invention, FIG. 5b—a top view on the fibre system illustrated in FIG. 5a, FIG. 6a—a perspective illustration of the fibre system of an embodiment of the intervertebral implant according to the invention, FIG. 6b—a top view on the fibre system illustrated in FIG. 6a, and FIG. 7—a section through a further embodiment of the intervertebral implant according to the invention.
Figure 2:
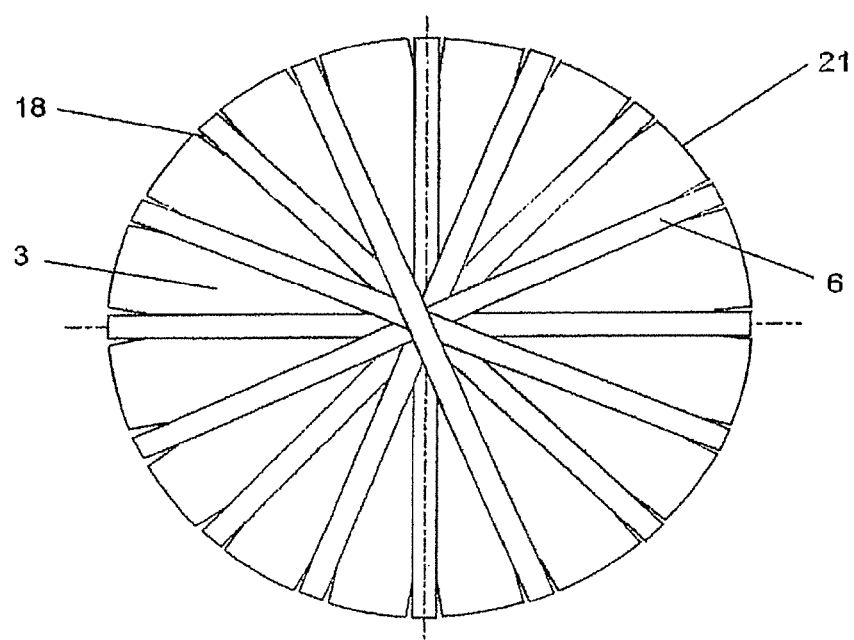

FIGS. 1 and 2 illustrate an embodiment of the intervertebral implant 1 according to the invention, that comprises a top cover plate 3 and a bottom cover plate 4, each with an external surface 7, 8 extending at right angles to the central axis 2 and having a lateral surface 21, 22 on the periphery. Between the cover plates 3, 4 there is a central part 10 provided with a central cavity 11 and a sheathing 12, that surrounds the fibre system 5. For the purpose of anchoring the fibres 6 of the fibre system 5 on the cover plates 3, 4, each of the peripheral lateral surfaces 21, 22 has grooves 18, distributed on the circumference and radially protruding into the lateral surfaces 21, 22, so that the fibre system 5 can be anchored in these grooves 18. In the central cavity 11 there is an elastically deformable formed body 9 with an incompressible core, preferably a liquid core 13. Due to the incompressibility of the liquid core 13 during a compression of the cover plates 3, 4 parallel to the longitudinal axis 2, for example, the elastic formed body 9 and the sheathing 12 with the fibre system 5 will bulge radially, i.e. at right angles to the longitudinal axis 2, consequently the fibres 6 will be under tension.

Figure 3:
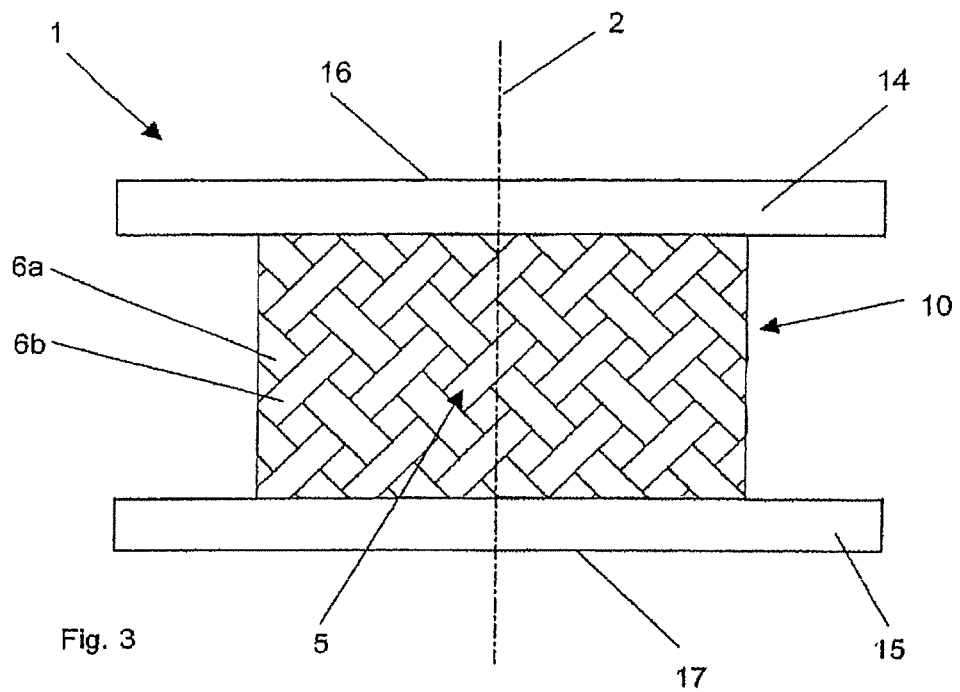
Figure 4:
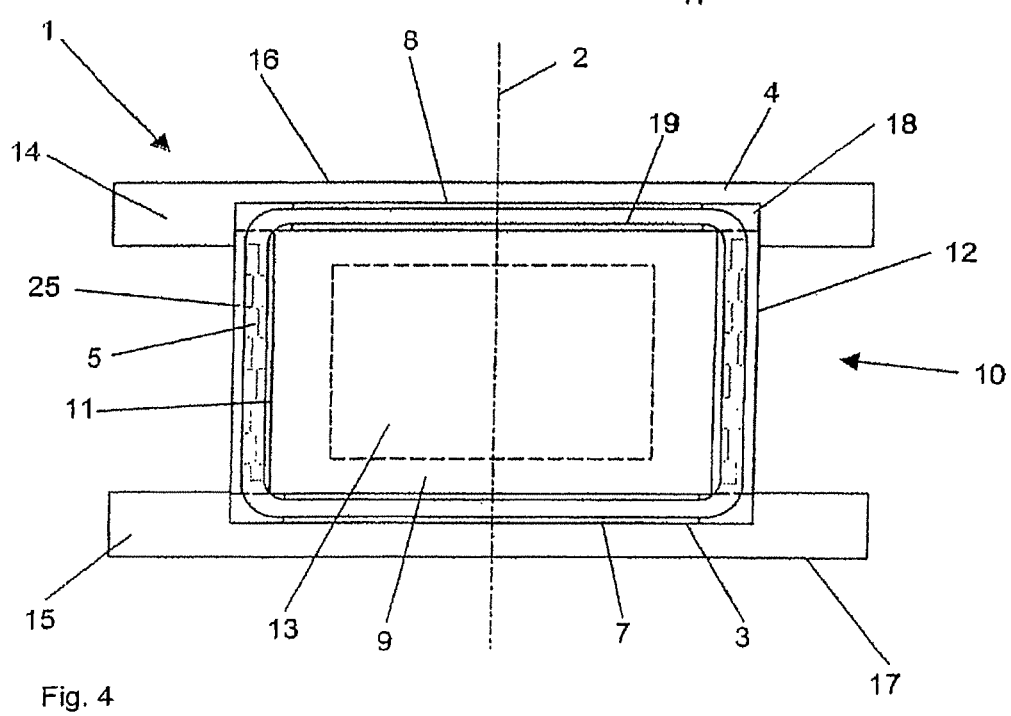

FIGS. 3 and 4 illustrate an embodiment of the intervertebral implant 1 according to the invention, that comprises two cover plates 3, 4, provided at right angles to the central axis 2, and an elastically deformable central part 10 situated between them. The central part 10 comprises a hollow-cylindrical sheathing 12 that is coaxial with the central axis 2 and a central cavity 11. In the central cavity 11 an elastic formed body 9 with an incompressible core is provided, preferably a liquid core 13. The formed body 9 is surrounded by a semipermeable membrane, whereas the sheathing 12, that surrounds the fibre system 5 and an elastic sheathing body 25 passed through by the fibre system 5, is made from a synthetic material. The closing plates 14, 15 are firmly joined with the cover plates 3, 4 and have axially protruding surfaces 16, 17, which can be brought to rest on the end plates of two adjacent bodies of the vertebra. The fibre system 5 is anchored on the cover plates 3, 4 and is integrated in the sheathing 12 and its purpose is to absorb the forces on the central part 10, said forces acting on the intervertebral implant 1 via the bodies of the vertebra adjacent to the closing plates 14, 15, i.e. torsional forces due to the rotation of the bodies of the vertebra about the central axis 2 relative to one another or bending moments due to lateral bending and/or flexion/extension of the spinal column. For example, a compression force, acting on the intervertebral implant 1 parallel to the central axis 2, is transferred by closing plates 14, 15 via both cover plates 3,4 to the central part 10, while as the result the elastic formed body 9 will bulge at right angles to the central axis 2. This expansion movement of the elastic formed body 9 is transferred to the sheathing 12 with the fibre system 5 and contained by this. Since the fibre system 5 is anchored on the cover plates 3, 4, the compression force, acting transversely to the central axis 2, generates tensile forces in the fibres of the fibre system 5. The fibre system 5 in this case is made from synthetic fibres, preferably from UHMWPE-fibres (ultra high molecular weight polyethylene) or from PET (polyethylene terephthalate) and comprises a mesh from first and second fibres 6a, 6b, that are interwoven with one another. By doing so, the first fibres 6a include an angle α and the second fibres 6b an angle β with the central axis 2. In the embodiment of the intervertebral implant 1 according to the invention illustrated here, the angles α and β are equal and are between 15° and 60°. The fibres 6a, 6b are anchored on the cover plates 3, 4 by means of grooves 18 that are arranged on the circumference of the cover plates 3, 4 parallel to the central axis 2, so that the fibres 6a, 6b are passed through the grooves 18 and can be guided to the next groove 18 over the surfaces 7, 8 in a channel 19. The cover plates 3, 4 are made from synthetic material, whereas the closing plates 14, 15, arranged externally, are made from titanium or a titanium alloy. The externally arranged closing plates 14, 15 are joined with the cover plates 3, 4 either by form-locking or frictional locking. In particular they can be adhered or welded to one another.

In FIGS. 5a and 5b a fibre system 5 is illustrated according to an embodiment of the intervertebral implant 1 according to the invention, wherein the fibres 6 extending over the end plates 3, 4 form chords on the circular surfaces 7, 8 of the cover plates 3, 4.

In FIGS. 6a and 6b a fibre system 5 is illustrated according to an embodiment of the intervertebral implant 1 according to the invention, wherein the fibres 6 extending over the end plates 3, 4 cross at the point of intersection of the central axis 2 and the end plates 3, 4.

When compared with the arrangement of the fibres 6 (FIGS. 6a, 6b), the guiding of the fibres 6 as chords (FIGS. 5a, 5b) over the surfaces 7, 8 of the end plates 3, 4 has the following advantages:

due to the better distribution of the crossing points of the fibres 6 no concentration will occur, especially between the external surfaces 7, 8 of the cover plates 3, 4 and the closing plates 14, 15 (FIGS. 3 and 4), and with the aid of a winding technique the fibre system 5 can be symmetrically produced relative the central axis 2 while the intervertebral implant 1 can be clamped in at the points of intersection between the central axis 2 and the cover plates 3, 4.

Figure 7:
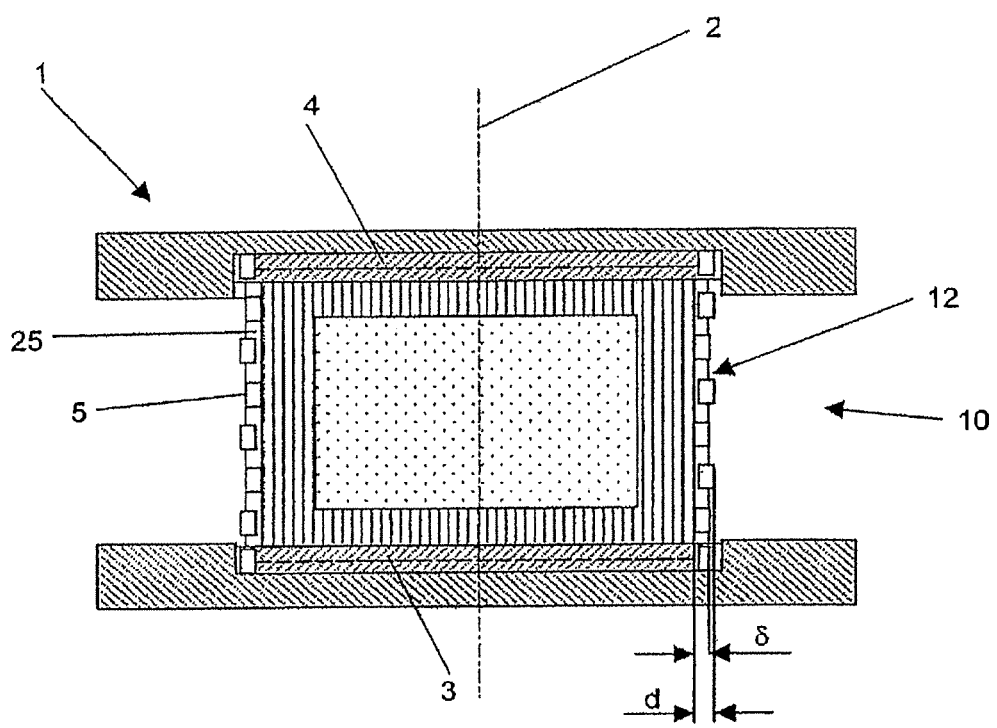

FIG. 7 illustrates an embodiment, that differs from the embodiment illustrated in FIGS. 3 and 4 only by that the periphery of the sheathing 12 provided on the central part 10 comprises an elastic sheathing body 25 only partially passed through by the fibre system 5, the thickness of the sheathing body d being smaller than the radial thickness δ of the fibre system.

What is claimed:

1. An intervertebral implant sized to be implanted between a lower endplate of an upper vertebra and an upper endplate of an adjacent lower vertebra, the implant comprising:
    (a) an upper closing plate having an external surface for contacting the lower endplate of the upper vertebra and an opposing inner surface;

(b) a lower closing plate having an external surface for contacting the upper endplate of the lower vertebra and an opposing inner surface;

(c) a top cover plate joined to the upper closing plate, the top cover plate including a top, outer surface and an opposing bottom, inner surface, wherein the outer surface of the top cover plate faces the inner surface of the upper closing plate;

(d) a bottom cover plate joined to the lower closing plate, the bottom cover plate including a bottom, outer surface and an opposing top, inner surface, wherein the outer surface of the bottom cover plate faces the inner surface of the lower closing plate;

(e) a deformable body located between the top and bottom cover plates having a first side wall located between the inner surfaces of the bottom and top cover plates, wherein the deformable body is a separate part from the top cover plate and from the bottom cover plate; and (f) a plurality of continuous, uninterrupted fibers, wherein the continuous, uninterrupted fibers are each wound along a fiber path that extends sequentially from beneath the inner surface of the top cover plate over a portion of the outer surface of the top cover plate between the inner surface of the upper closing plate and the outer surface of the top cover plate and back past the inner surface of the top cover plate and traversing the first side wall and past the inner surface of the bottom cover plate over a portion of the outer surface of the bottom cover plate between the inner surface of the lower closing plate and the outer surface of the bottom cover plate and back past the inner surface of the bottom cover plate and traversing the first side wall in the direction back towards the top cover plate, and wherein the continuous, uninterrupted fibers are located entirely between the inner surfaces of the upper and lower closing plates.

2. The intervertebral implant of claim 1 wherein the continuous, uninterrupted fibers are located directly adjacent to the outer surface of the bottom cover plate and also directly adjacent to the outer surface of the top cover plate.

3. The intervertebral implant of claim 1 wherein the upper and lower closing plates are manufactured from titanium or titanium alloy.

4. The intervertebral implant of claim 1 wherein the continuous, uninterrupted fibers comprise a yarn.

5. The intervertebral implant of claim 1 further comprising a sheathing that circumferentially surrounds the portion of the continuous, uninterrupted fibers that traverse the first side wall.

6. The intervertebral implant of claim 1 wherein the deformable body is elastically deformable.

7. The intervertebral implant of claim 1 wherein the continuous, uninterrupted fibers hold together the top and bottom cover plates and the deformable body.

8. The intervertebral implant of claim 1 wherein the top cover plate is joined to the upper closing plate by frictional locking or form-locking.

9. The intervertebral implant of claim 1 wherein the top cover plate is joined to the upper closing plate by welding.

10. An intervertebral implant sized to be implanted between a lower endplate of an upper vertebra and an upper endplate of an adjacent lower vertebra, the implant comprising:

(a) an upper closing plate having an external surface for contacting the lower endplate of the upper vertebra and an opposing inner surface;

(b) a lower closing plate having an external surface for contacting the upper endplate of the lower vertebra and an opposing inner surface;

(c) a top cover plate joined to the upper closing plate, the top cover plate including a top, outer surface and an opposing bottom, inner surface, wherein the outer surface of the top cover plate faces the inner surface of the upper closing plate;

(d) a bottom cover plate joined to the lower closing plate, the bottom cover plate including a bottom, outer surface and an opposing top, inner surface, wherein the outer surface of the bottom cover plate faces the inner surface of the lower closing plate;

(e) a deformable body located between the top and bottom cover plates having a first side wall located between the inner surfaces of the bottom and top cover plates, wherein the deformable body is a separate part from the top cover plate and from the bottom cover plate; and (f) a first and a second continuous, uninterrupted fiber, wherein each of the first and second continuous, uninterrupted fibers are wound along a fiber path that extends sequentially from beneath the inner surface of the top cover plate over a portion of the outer surface of the top cover plate between the inner surface of the upper closing plate and the outer surface of the top cover plate and back past the inner surface of the top cover plate and traversing the first side wall and past the inner surface of the bottom cover plate over a portion of the outer surface of the bottom cover plate between the inner surface of the lower closing plate and the outer surface of the bottom cover plate and back past the inner surface of the bottom cover plate and traversing the first side wall in the direction back towards the top cover plate, and again passing from beneath the inner surface of the top cover plate and over a portion of the outer surface of the top cover plate between the inner surface of the upper closing plate and the outer surface of the top cover plate and back past the inner surface of the top cover plate;

wherein the first and second continuous, uninterrupted fibers are located entirely between the inner surfaces of the upper and lower closing plates.

11. The intervertebral implant of claim 10 wherein the first and second continuous, uninterrupted fibers are each located directly adjacent to the outer surface of the bottom cover plate and also directly adjacent to the outer surface of the top cover plate.

12. The intervertebral implant of claim 10 wherein the upper and lower closing plates are manufactured from titanium or titanium alloy.

13. The intervertebral implant of claim 10 wherein the first and second continuous, uninterrupted fibers each comprise a yarn.

14. The intervertebral implant of claim 10 further comprising a sheathing that circumferentially surrounds the portion of the first and second continuous, uninterrupted fibers that traverse the first side wall.

15. The intervertebral implant of claim 10 wherein the deformable body is elastically deformable.

16. The intervertebral implant of claim 10 wherein the first and second continuous, uninterrupted fibers hold together the top and bottom cover plates and the deformable body.

17. The intervertebral implant of claim 10 wherein the top cover plate is joined to the upper closing plate by frictional locking or form-locking 18. The intervertebral implant of claim 10 wherein the top cover plate is joined to the upper closing plate by welding.

\* \* \* \* \*